US008840248B2

(12) United States Patent
Imamura (10) Patent No.: US 8,840,248 B2
(45) Date of Patent: Sep. 23, 2014

(54) IMAGE PROCESSING APPARATUS, IMAGE PROCESSING METHOD AND STORAGE MEDIUM

(75) Inventor: Hiroshi Imamura, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 13/349,944

(22) Filed: Jan. 13, 2012

(65) Prior Publication Data

US 2012/0194782 A1 Aug. 2, 2012

(30) Foreign Application Priority Data

Feb. 1, 2011 (JP) ................. 2011-020089

(51) Int. Cl.
*A61B 3/14* (2006.01)
*A61B 3/00* (2006.01)
*G06T 7/00* (2006.01)

(52) U.S. Cl.
CPC ........... *G06T 7/0012* (2013.01); *G06T 2210/41* (2013.01); *G06T 2207/10101* (2013.01); *G06T 2207/30041* (2013.01)
USPC .......................................... 351/206; 351/246

(58) Field of Classification Search
USPC ................................................ 351/206, 246
See application file for complete search history.

(56) References Cited

U.S. PATENT DOCUMENTS

| 7,641,339 B2 | 1/2010 | Hangai et al. |
| 8,474,978 B2 | 7/2013 | Huang et al. |
| 2007/0216909 A1* | 9/2007 | Everett et al. ................. 356/479 |
| 2008/0309881 A1* | 12/2008 | Huang et al. ................. 351/246 |
| 2009/0033870 A1 | 2/2009 | Hangai et al. |
| 2011/0137157 A1 | 6/2011 | Imamura et al. |
| 2012/0063660 A1 | 3/2012 | Imamura et al. |

FOREIGN PATENT DOCUMENTS

| CN | 101778593 A | 7/2010 |
| EP | 2022391 A1 | 2/2009 |
| JP | 2009-034480 A | 2/2009 |
| WO | 2008/157406 A1 | 12/2008 |

OTHER PUBLICATIONS

Apr. 18, 2012 European Search Report in European Patent Appln. No. 12151688.4.
Feb. 20, 2014 Chinese Official Action in Chinese Patent Appln. No. 201210023479.1.

* cited by examiner

*Primary Examiner* — Scott J Sugarman
*Assistant Examiner* — Mustak Choudhury
(74) *Attorney, Agent, or Firm* — Fitzpatrick, Cella, Harper & Scinto

(57) ABSTRACT

An image processing apparatus includes: an acquisition unit configured to acquire a tomogram of an eye portion of a patient to be examined; an information acquisition unit configured to acquire information of a predetermined portion and position information of a predetermined tissue structure from the tomogram; and a calculation unit configured to calculate an evaluation value based on a relationship between the information of the predetermined portion and a position of the predetermined tissue structure.

13 Claims, 9 Drawing Sheets

IMAGE PROCESSING APPARATUS, IMAGE PROCESSING METHOD AND STORAGE MEDIUM

BACKGROUND OF THE INVENTION

1. Field of the Invention

The present invention relates to an image processing apparatus, an image processing method, and a storage medium.

2. Description of the Related Art

Figure 10A:
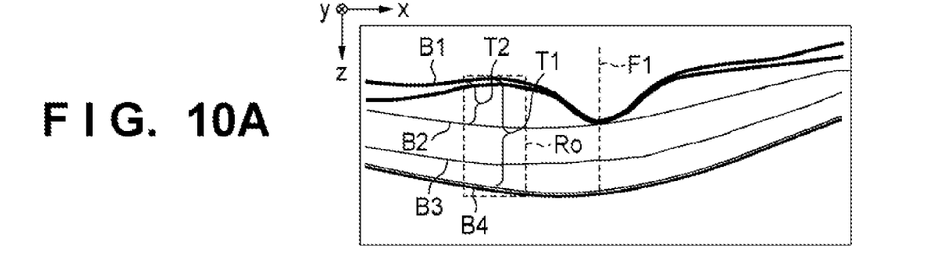
FIGS. 10A to 10D are views associated with a tomogram of a macular region of a retina captured by an OCT.
Figure 10B:
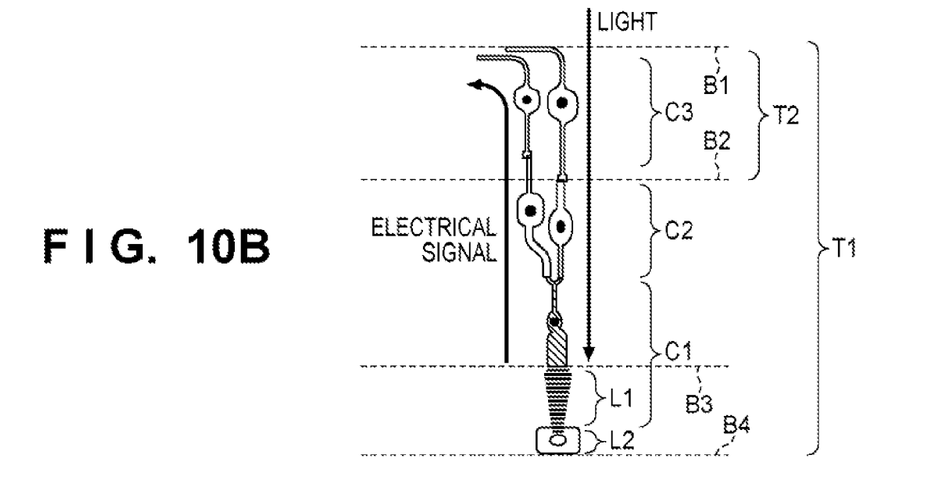

Ophthalmic examinations are prevalently made for the purpose of earlier diagnoses of various diseases that come before lifestyle-related diseases and causes of blindness. An ophthalmic tomography apparatus such as an OCT (Optical Coherence Tomography) is expected to be helpful to give more adequate diagnoses of diseases since it allows to three-dimensionally observe the state of the interior of retina layers. In order to quantitatively measure thicknesses of layers, boundaries of respective retina layers are detected from a tomogram using a computer. For example, as shown in FIG. 10B, an inner limiting membrane B1, inner plexiform layer boundary B2, boundary B3 between photoreceptor inner and outer segments, and retinal pigment epithelium boundary B4 are detected, and retina thicknesses T1 and GCC (Ganglion Cell Complex) thicknesses T2 are measured.

Figure 10C:
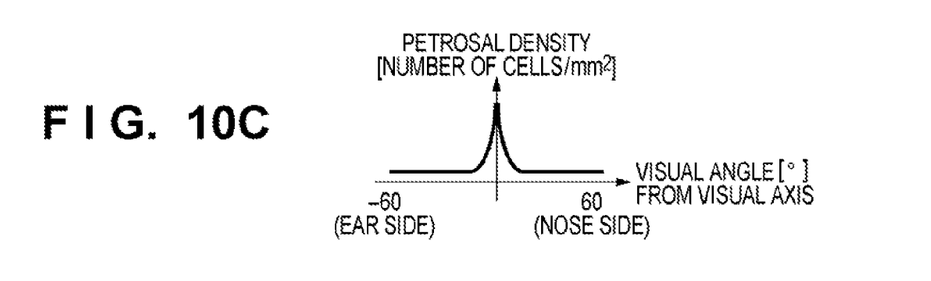

Tomograms of an eye portion captured using the OCT include regions (cells, tissues, portions) which influence a visual function, and a doctor observes conditions of damages of corresponding cells, layer thicknesses, and positional relationships with a portion such as a fovea centralis F1 (FIG. 10A) upon predicting the restoration possibility and prognosis of the visual function. For example, FIG. 10B shows an enlarged view of a region Ro in FIG. 10A. Light which has reached a retina is converted into an electrical signal by an outer segment L1 of a photoreceptor cell C1, and is perceived by a visual cortex (not shown) of the cerebrum via a bipolar cell C2, a ganglion cell C3 and optic nerve (not shown) in turn. If the photoreceptor outer segment L1 is damaged, since it can no longer convert light into an electrical signal, the visual function lowers at the damaged portion. The photoreceptor cell C1 includes a petrosa and rod, and the petrosa controls the visual function in a bright place. As shown in FIG. 10C, since the petrosa is present at a higher density as it is closer to the fovea centralis F1, the influence of the photoreceptor outer segment damage on the visual function per unit area is greater as it is closer to the fovea centralis F1. Note that a visual axis is a line which connects an object to be gazed and the fovea centralis F1. Therefore, in order to estimate the influence of the photoreceptor outer segment damage on the visual function, a degree of damage (length of the outer segment) at the position of the photoreceptor outer segment damage, an existence range (area) of the damage region, and a distance of the damage region from the fovea centralis have to be taken into consideration.

Figure 10D:
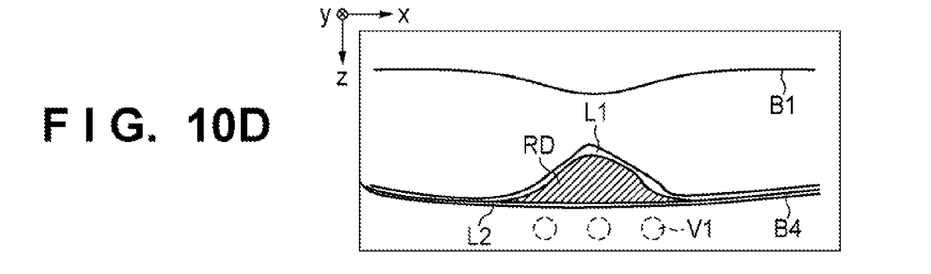

Furthermore, since the photoreceptor cell C1 derives nutrition from choroidal vessels V1, as shown in FIG. 10D, if a lesion such as an amotio retinae RD exists between the photoreceptor outer segment L1 and a retinal pigment epithelium L2, nutrition cannot be supplied to the photoreceptor cell C1. Therefore, if the amotio retinae RD exists, the visual function is more likely to decrease in the future. If existence of the amotio retinae RD is protracted, the photoreceptor cell C1 becomes extinct, and the visual function can no longer be restored. Therefore, in order to estimate the influence on the visual function or to predict the prognosis of the visual function from the retina shape, not only the thicknesses of cells and layers are simply measured, but also the positional relationships with a portion such as the fovea centralis F1, and the presence/absence or existence period of a lesion such as the amotio retinae RD have to be taken into consideration. For the purpose of diagnosis support of a glaucoma and optic nerve disease, a technique of measuring the GCC thicknesses T2 related to a visual field as one of the visual functions, and displaying differences from GCC thicknesses T2 in a healthy eye as a map is disclosed in WO/2008/157406 (to be referred to as literature 1 hereinafter).

However, the technique described in literature 1 assumes an application to a glaucoma, and does not consider any positional relationship with the fovea centralis F1 and any influence of an exudative lesion on the visual function, which are to be considered in case of a macular disease. Also, the technique described in literature 1 presents only one or more layer thickness maps (parallelly) for predictions of the restoration possibility and prognosis of the visual function, and the restoration possibility and prognosis of the visual function have to be visually judged from the maps.

Also, a technique described in Japanese Patent Laid-Open No. 2009-34480 is premised on the presence of test results of a perimeter, and measures layer thicknesses of a portion, the anomaly of which was revealed by the visual field test to examine correspondence with visual function evaluation values by the visual field test. As is known, a change in retina shape appears prior to a change in visual function, and it is desirable to predict the prognosis based only on information obtained from ophthalmic tomograms in terms of early detection of a retinal disease.

SUMMARY OF THE INVENTION

The present invention provides an image processing technique which determines an influence degree on a visual function using only an ophthalmic tomogram by quantitating positional relationships with a predetermined portion and a distribution condition of lesion locations, and can provide this determination result as diagnosis support information.

According to one aspect of the present invention, there is provided an image processing apparatus comprising: an acquisition unit configured to acquire a tomogram of an eye portion of a patient to be examined; an information acquisition unit configured to acquire information of a predetermined portion and position information of a predetermined tissue structure from the tomogram; and a calculation unit configured to calculate an evaluation value based on a relationship between the information of the predetermined portion and a position of the predetermined tissue structure.

According to the arrangement of the present invention, an influence degree on a visual function is determined using only an ophthalmic tomogram by quantitating positional relationships with a predetermined portion and a distribution condition of lesion locations, and this determination result can be provided as diagnosis support information.

Further features of the present invention will become apparent from the following description of exemplary embodiments (with reference to the attached drawings).

DESCRIPTION OF THE EMBODIMENTS (First Embodiment)

An image processing apparatus according to this embodiment is configured to predict the influence on a visual function and the prognosis of the visual function based on the positional relationship between a thinned region of photoreceptor outer segment thicknesses and a fovea centralis F1, the presence/absence of an amotio retinae RD, and the like. An image processing apparatus according to embodiments of the present invention and an image processing method in the image processing apparatus will be described hereinafter with reference to the accompanying drawings.

Figure 12:
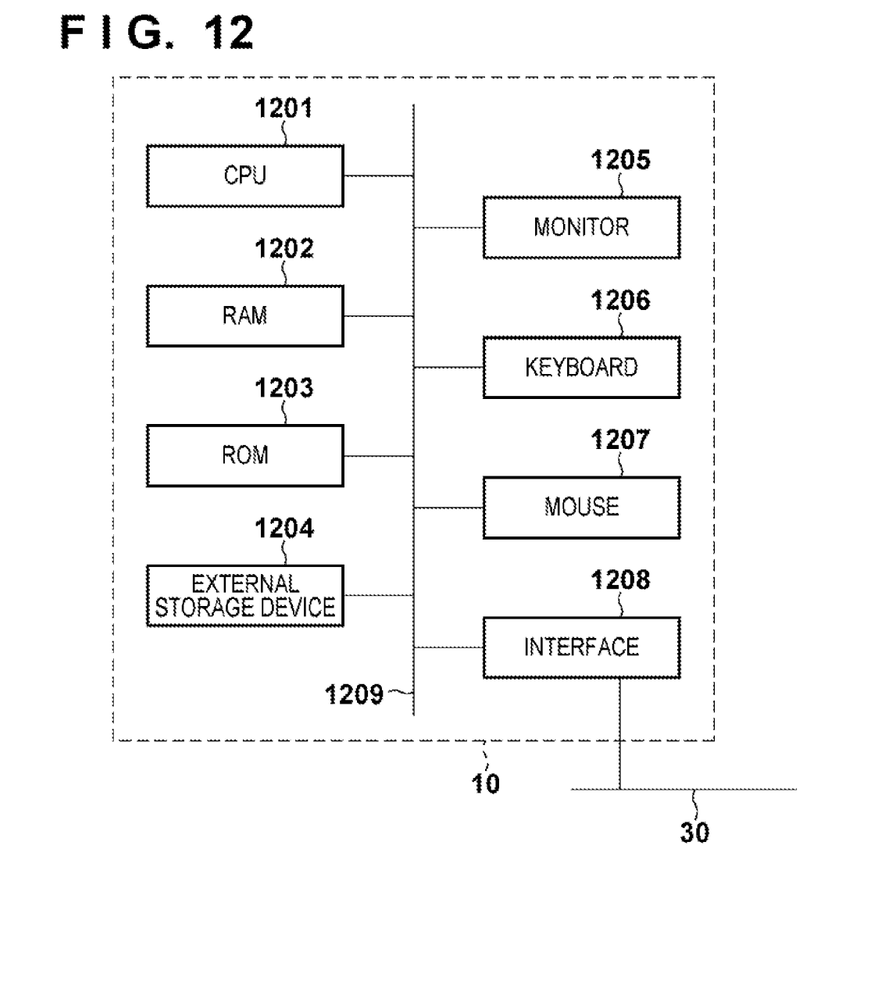
FIG. 12 is a block diagram showing an example of the hardware arrangement of the image processing apparatus.

FIG. 12 is a block diagram showing an example of the hardware arrangement of an image processing apparatus 10. A CPU 1201 controls the overall operations of the image processing apparatus 10. A ROM 1203 and external storage device 1204 store programs which are executable by the image processing apparatus 10, and parameters. A RAM 1202 serves as a work area used when programs are executed. A monitor 1205 serves as an output unit, and displays image processing results and calculation processing results. A keyboard 1206 and mouse 1207 serve as an input unit. The user can input various commands to the image processing apparatus via the keyboard 1206 and mouse 1207. An interface 1208 connects the image processing apparatus 10 to a network (LAN) 30. The respective components shown in FIG. 12 are connected via a bus 1209.

Figure 11:
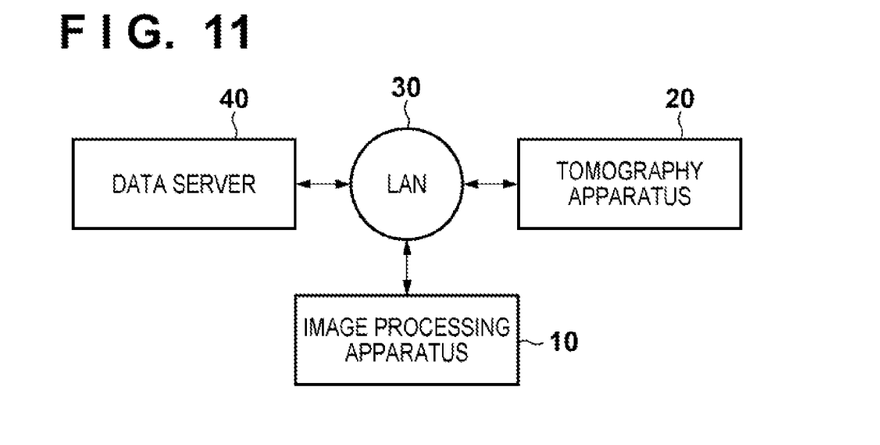
FIG. 11 is a diagram showing an example of the configuration of a system including the image processing apparatus according to the embodiment.

FIG. 11 is a diagram showing the configuration of apparatuses which are connectable to the image processing apparatus 10. A tomography apparatus 20 is connectable to a data server 40 via the network (LAN) 30 such as Ethernet®. The image processing apparatus 10 is connectable to the tomography apparatus 20 via the network (LAN) 30 or an interface such as an optical fiber, USB, or IEEE1394. The tomography apparatus 20 is an apparatus for capturing ophthalmic tomograms, and is, for example, a time-domain or Fourier-domain OCT. The tomography apparatus 20 three-dimensionally captures tomograms of an eye to be examined (not shown) in response to an operation by an operator (not shown). The captured tomograms are transmitted to the image processing apparatus 10. The data server 40 is a server, which holds the tomograms, image feature amounts, and the like of the eye to be examined, and saves the tomograms of the eye to be examined output from the tomography apparatus 20 and analysis results output from the image processing apparatus 10. Also, in response to a request from the image processing apparatus 10, the data server 40 transmits previous data associated with the eye to be examined to the image processing apparatus 10.

Note that this embodiment will explain a case in which the image processing apparatus 10 measures a boundary B3 between photoreceptor inner and outer segments, and retinal pigment epithelium boundary B4. However, the present invention is not limited to this. The image processing apparatus 10 can detect other layer boundaries (an external limiting membrane (not shown), an inner boundary of a stratum pigmenti bulbi (not shown), and the like.

Figure 1:
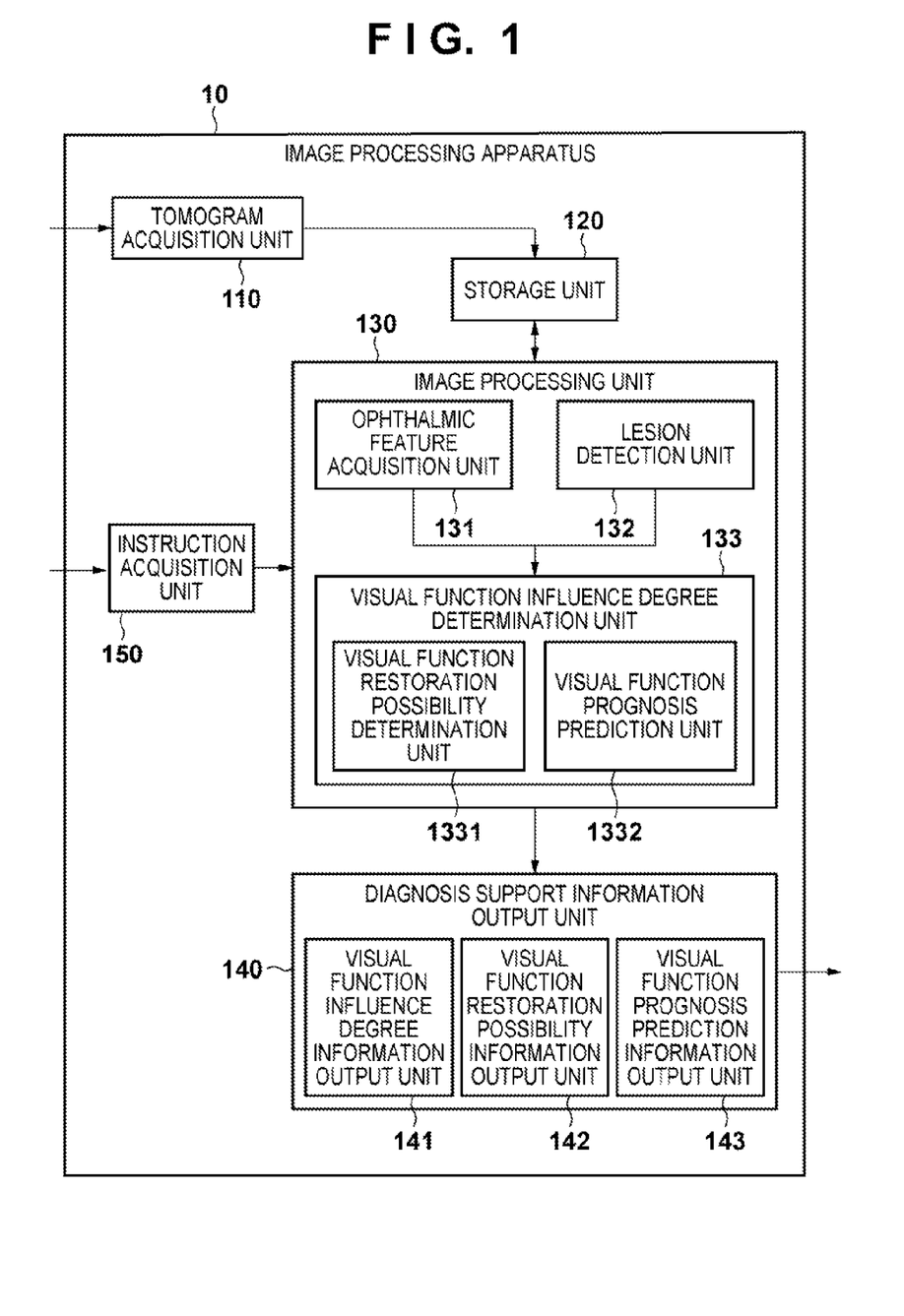
FIG. 1 is a block diagram showing an example of the functional arrangement of an image processing apparatus according to the first embodiment.

FIG. 1 is a block diagram showing an example of the functional arrangement of the image processing apparatus 10. The image processing apparatus 10 includes a tomogram acquisition unit 110, storage unit 120, image processing unit 130, diagnosis support information output unit 140, and instruction acquisition unit 150. The image processing unit 130 includes an ophthalmic feature acquisition unit 131, lesion detection unit 132, and visual function influence degree determination unit 133. The visual function influence degree determination unit 133 includes a visual function restoration possibility determination unit 1331 and visual function prognosis prediction unit 1332. The diagnosis support information output unit 140 includes a visual function influence degree information output unit 141, visual function restoration possibility information output unit 142, and visual function prognosis prediction information output unit 143.

Figure 2:
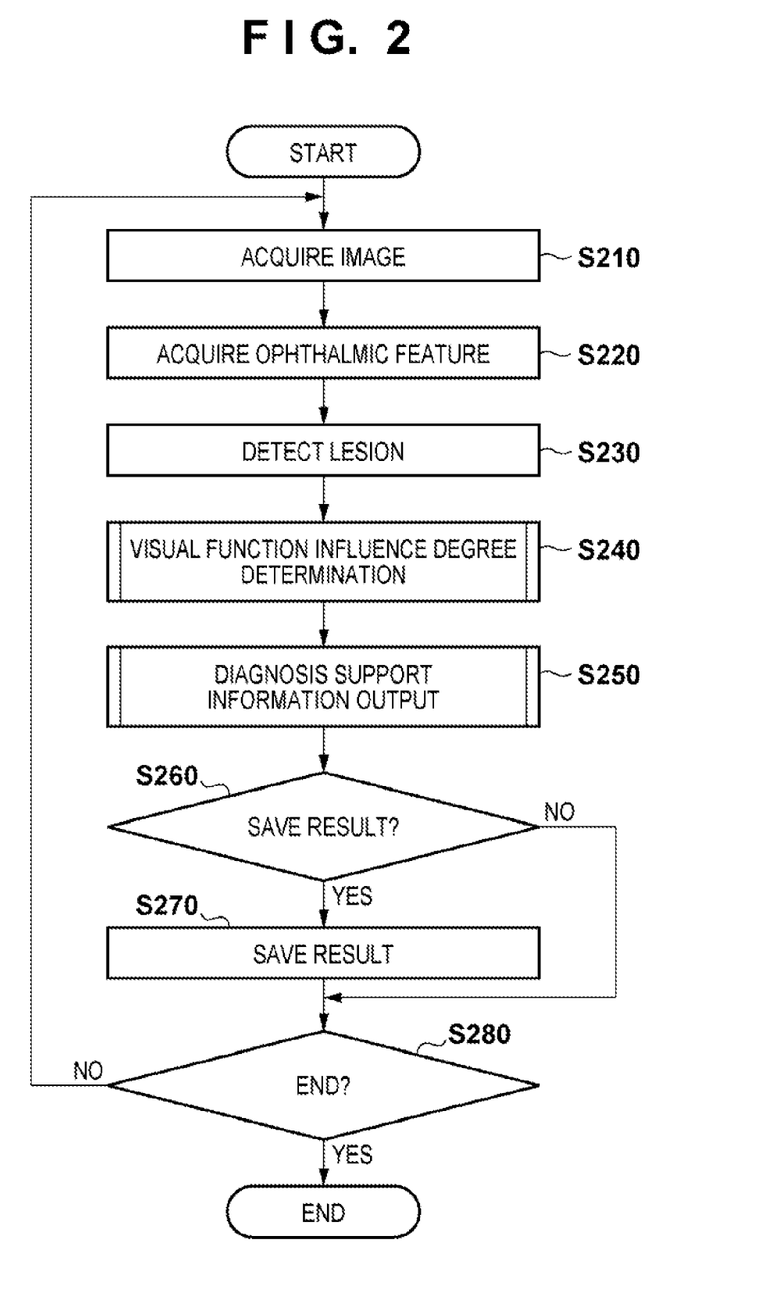
FIG. 2 is a flowchart showing the sequence of processing to be executed by the image processing apparatus according to the first embodiment.

The functions of respective blocks included in the image processing apparatus 10 will be described below in association with a practical execution sequence of the image processing method in the image processing apparatus 10 shown in the flowchart of FIG. 2. In step S210, the tomogram acquisition unit 110 transmits a tomogram acquisition request to the tomography apparatus 20. The tomography apparatus 20 transmits corresponding tomograms in response to the acquisition request. The tomogram acquisition unit 110 receives the tomograms corresponding to the acquisition request from the tomography apparatus 20 via the network 30. The tomogram acquisition unit 110 stores the received tomograms in the storage unit 120.

In step S220, the ophthalmic feature acquisition unit 131 acquires information of predetermined portions and position information of predetermined tissue structures from tomograms. The ophthalmic feature acquisition unit 131 acquires ophthalmic features (anatomic features), which represent predetermined cells, issues, or portions, from the tomograms. The ophthalmic feature acquisition unit 131 can detect, as ophthalmic features, for example, an inner limiting membrane B1, boundary B3 between photoreceptor inner and outer segments, and retinal pigment epithelium boundary B4 from the tomograms stored in the storage unit 120. The ophthalmic feature acquisition unit 131 then stores the detected features in the storage unit 120.

A practical ophthalmic feature acquisition sequence will be explained below. A processing method for detection of boundaries of respective retina layers will be explained first. In this case, a volume image to be processed is considered as a set of two-dimensional tomograms (B-scan images), and the following processing is applied to respective two-dimensional tomograms. A two-dimensional tomogram of interest undergoes smoothing processing to remove noise components. Next, edge components are detected from the two-dimensional tomogram, and some line segments are extracted as candidates of layer boundaries based on their connectivity. Then, from the extracted candidates of layer boundaries, the uppermost line segment is selected as the inner limiting membrane B1. Also, the line segment, which is located on the outer layer side (the larger z-coordinate side in FIG. 10A) of the inner limiting membrane B1 and has a maximum contrast, is selected as the boundary B3 between photoreceptor inner and outer segments. Furthermore, the lowermost line segment of the extracted candidates is selected as the retinal pigment epithelium boundary B4.

Furthermore, layer boundaries may be precisely extracted by applying a deformable model such as Snakes or a level-set method to have these line segments as initial values. Also, layer boundaries may be detected by a graph cut method. Note that boundary detection using the deformable model or graph cut method may be three-dimensionally executed for a volume image, or may be two-dimensionally executed for respective two-dimensional tomograms. Also, arbitrary layer boundary detection methods may be used as long as they can detect layer boundaries from an ophthalmic tomogram.

In step S230, the lesion detection unit 132 detects the presence/absence of lesion candidates (amotio retinae) within a region defined by the ophthalmic features acquired in step S220, for example, within a region sandwiched between the boundary B3 between photoreceptor inner and outer segments and the retinal pigment epithelium boundary B4. Note that this embodiment will describe a case in which the amotio retinae RD exists below a fovea centralis. The amotio retinae RD is likely to develop at every location in an eye fundus other than a Mariotte blind spot, and the image processing method of this embodiment is applicable to a case in which the amotio retinae RD has developed in an arbitrary location (except for the Mariotte blind spot) within a capturing range of the tomograms.

Figure 3A:
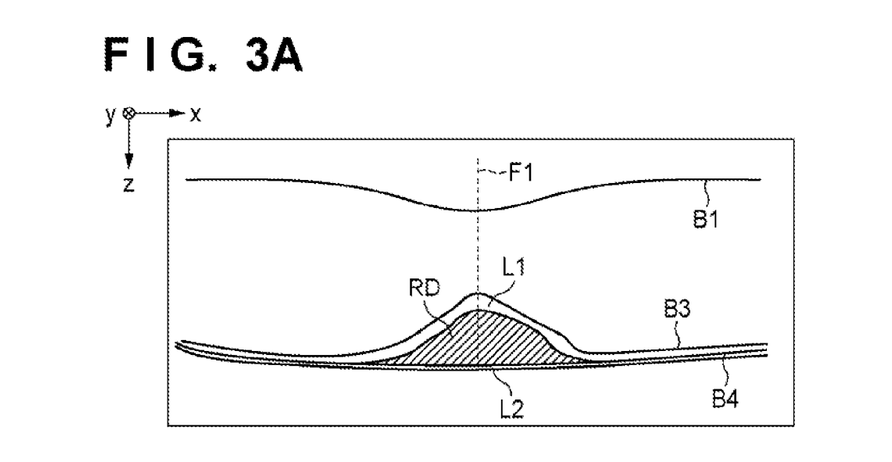
FIGS. 3A to 3C are views for explaining the image processing contents in the first embodiment.
Figure 3B:
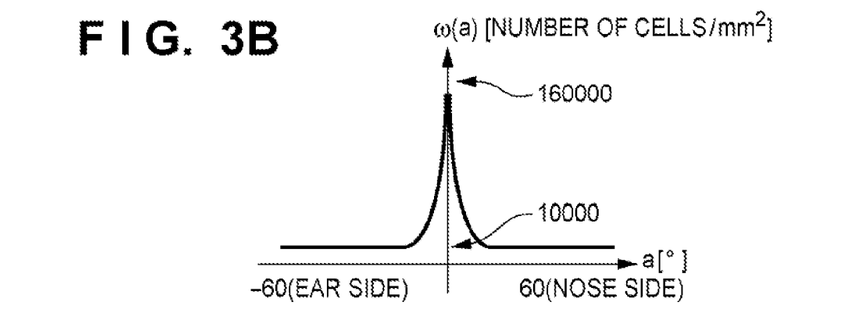
Figure 3C:
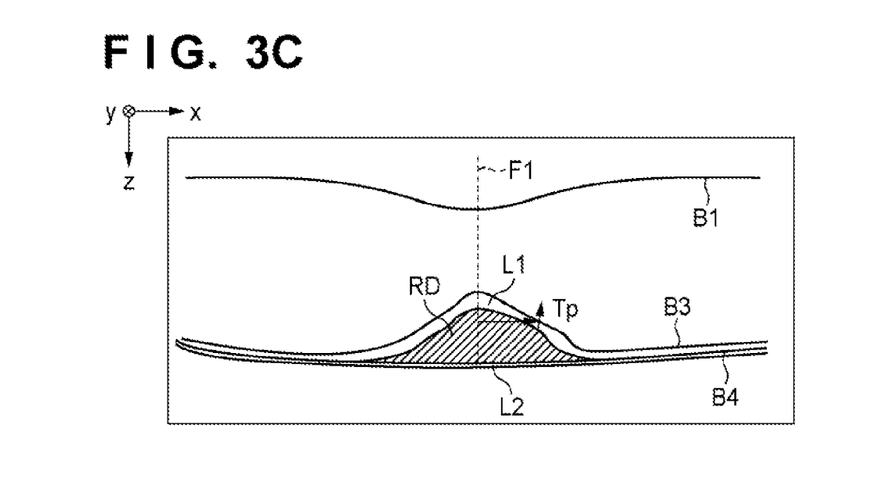

A detection method of the amotio retinae RD will be described below. Lesion candidate regions are detected by comparing luminance levels in the region defined by the ophthalmic features (anatomic features) with a predetermined luminance threshold Trd. For example, regions which assume lower luminance values than the threshold are detected as lesion candidates. As shown in FIGS. 3A and 3C, low-luminance regions, which are located within a region, which is located on the outer layer side (the larger z-coordinate side) of the boundary B3 between photoreceptor inner and outer segments and on the inner layer side (the smaller z-coordinate side) of the retinal pigment epithelium boundary B4 on respective A-scan lines in the x-axis direction on an x-z plane, are extracted as lesion candidate regions. As the extraction method, a known extraction method is applicable. In this case, regions having lower luminance values than the luminance threshold Trd within the aforementioned region are detected as amotio retinae candidate regions (lesion candidate regions).

The lesion detection unit 132 quantitates sizes of portions responsible for the visual function based on the ophthalmic features (the fovea centralis F1, inner limiting membrane B1, boundary B3 between photoreceptor inner and outer segments, and retinal pigment epithelium boundary B4) and the positions of the lesion candidates (amotio retinae RD). The lesion detection unit 132 measures (quantitates) thicknesses (photoreceptor outer segment thicknesses) Tp(x, y) of a photoreceptor outer segment L1 at respective coordinate points within an x-y plane, as a relationship between the positions and sizes. The photoreceptor outer segment L1 responsible for the visual function converts light, which has reached the retina of an eye portion of a patient to be examined, into an electrical signal, so as to control the visual function. In this case, as a simple measurement method of Tp(x, y), values obtained by subtracting distances in the z-axis direction of the amotio retinae region from a distance in the z-axis direction between the boundary B3 between photoreceptor inner and outer segments and the retinal pigment epithelium boundary B4 on respective A-scan lines in the x-axis direction on the x-z plane are used. Note that the measurement method of the thicknesses of the photoreceptor outer segment L1 is not limited to this. For example, the inner boundary of the stratum pigmenti bulbi (not shown) may be extracted in step S220, and values obtained by subtracting the amotio retinae thicknesses from the distance between the boundary B3 between photoreceptor inner and outer segments and the inner boundary of the stratum pigmenti bulbi (not shown) may be used as Tp(x, y).

Next, the lesion detection unit 132 acquires a normal value Tn of the photoreceptor outer segment thickness, and normal value data (see FIG. 3B) associated with a density distribution $\omega(a)$ [the number of cells/mm$^2$] of photoreceptor cells within the x-y plane from the data server 40. In this case, the lesion detection unit 132 acquires data associated with the petrosal of the photoreceptor cells. An abscissa is a visual angle [°] from a visual axis (a line which connects a crystalline lens and the fovea centralis).

In step S240, the visual function influence degree determination unit 133 calculates evaluation values from the relationship between the information of the predetermined portions and the positions of the predetermined issue structures. The visual function influence degree determination unit 133 calculates influence degrees on the visual function using the thicknesses (photoreceptor outer segment thicknesses) Tp(x, y) of the photoreceptor outer segment L1 quantitated in association with the portions responsible for the visual function. In this step, determination of a restoration possibility of the visual function, and that of a possibility of a visual function drop (prognosis prediction) can also be made together. Details of this step will be explained later with reference to FIG. 4.

In step S250, the diagnosis support information output unit 140 outputs the determination result of the visual function influence degree determination unit 133 as diagnosis support information. The diagnosis support information output unit 140 generates a two-dimensional coordinate map (visual function influence degree map) which has values of the influence degrees calculated in the determination step S240 as pixel values of the tomogram, and outputs that map as the diagnosis support information. Also, the diagnosis support information output unit 140 can generate a two-dimensional coordinate map (visual function restoration possibility map) which has indices (values) indicating restoration possibilities of the visual function as pixel values of the tomogram, and can output that map as the diagnosis support information. Furthermore, the diagnosis support information output unit 140 can generate a two-dimensional coordinate map (visual function drop risk degree map) having indices (values) indicating visual function drop possibilities as pixel values of the tomogram, and can output that map as the diagnosis support information. In this case, the visual function influence degree map, visual function restoration possibility map, and visual function drop risk degree map are included in the diagnosis support information, and determination results of the visual function influence degree determination unit 133 are visualized by display control for displaying those determination results on the two-dimensional coordinate maps.

In step S260, the instruction acquisition unit 150 externally acquires an instruction as to whether or not to save the current processing results associated with the eye to be examined in the data server 40. This instruction is input by the operator via, for example, the keyboard 1206 and mouse 1207 shown in FIG. 12. If the processing result save instruction is issued, the process advances to step S270; otherwise, the process jumps to step S280.

In step S270, the diagnosis support information output unit 140 transmits a date and time of inspection, identification information required to identify the eye to be examined, the tomograms, the analysis results of the image processing unit 130, and the diagnosis support information obtained by the diagnosis support information output unit 140 to the data server 40 in association with each other.

In step S280, the instruction acquisition unit 150 externally acquires an instruction as to whether or not to end the tomogram analysis processing by the image processing apparatus 10. This instruction is input by the operator via the keyboard 1206 and mouse 1207 shown in FIG. 12. If the processing end instruction is acquired, the analysis processing ends. On the other hand, if a processing continue instruction is acquired, the process returns to step S210 to execute processing for the next eye to be examined (or re-processing for the same eye to be examined).

(Visual Function Influence Degree Determination Processing)

Figure 4:
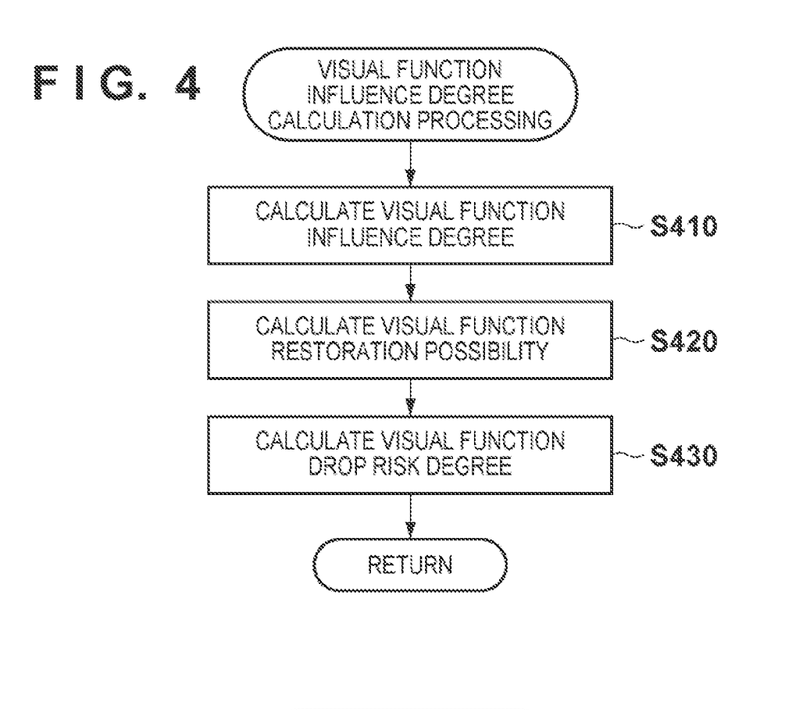
FIG. 4 is a flowchart showing details of processing executed in step S240 according to the first embodiment.

Details of the processing executed in step S240 will be described below with reference to FIG. 4. In step S410, the visual function influence degree determination unit 133 calculates ratios (Tn/Tp) of the normal value data associated with the size of a portion responsible for the visual function, which size is quantitated by the lesion detection unit 132, to the sizes Tp(x, y) of that portion. Then, the visual function influence degree determination unit 133 calculates a value indicating an influence degree by multiplying the normal value data ($\omega(a)$) indicating the density distribution of the photoreceptor cells by the ratios. The visual function influence degree determination unit 133 can acquire the normal value data (Tn) associated with the size of the portion responsible for the visual function, and the data ($\omega(a)$) indicating the density distribution of the photoreceptor cells from, for example, the data server 40. More specifically, the visual function influence degree determination unit 133 calculates an influence degree $S_1$ on the visual function by equation (1) below. The calculation of the value indicating the influence degree on the visual function uses the photoreceptor outer segment thicknesses Tp(x, y) at respective points on the x-y plane detected in step S230, the normal value Tn associated with the position and shape (for example, the thickness) of the photoreceptor outer segment, and the normal value data associated with the density distribution $\omega(a)$ of the photoreceptor cells within the x-y plane. In this case, a visual acuity will be examined as the visual function.

$$S_1 = \Sigma\{\omega(a) \cdot Tn/Tp(x,y)\} \qquad (1)$$

where Tp(x, y)/Tn represents a degree of thinning of a petrosal outer segment, and Tn=60 μm in this embodiment. As can be understood from equation (1), the influence degree on the visual function is larger as a thinned region of the petrosal outer segment is broader, and as a distance between the thinned region and fovea centralis is smaller.

In step S420, the visual function restoration possibility determination unit 1331 determines a visual function restoration possibility $R_1$ at respective points (x, y) on the x-y plane from the ratios between the photoreceptor outer segment thicknesses obtained in step S230 and the normal value of the photoreceptor outer segment thickness, as given by:

$$R_1 = \Sigma\{A\} \qquad (2)$$

$$A = \begin{cases} \left(\frac{Tp(x,y)}{Tn}\right) \cdot \left(\frac{1}{RD(t)}\right) & \left(\frac{Tp(x,y)}{Tn} \geq Tr\right) \\ 0 & \frac{Tp(x,y)}{Tn} < Tr \end{cases} \qquad (2')$$

where RD(t) is an existence period of the amotio retinae.

If the ratio Tp/Tn is less than a threshold associated with the ratio (<Tr), the visual function restoration possibility determination unit 1331 determines that it is difficult to restore the photoreceptor outer segment, and calculates an index (value) indicating the restoration possibility of the visual function at that position (x, y) as zero. If Tp/Tn is equal to or larger than the threshold associated with the ratio (≥Tr), the visual function restoration possibility is calculated by equation (2'). Also, since it is considered that the photoreceptor cells have poorer nutrition as the existence period of the lesion candidate (the existence period RD(t) of the amotio retinae RD) is longer, $R_1$ assumes a smaller value since it is multiplied by (1/the existence period (RD(t)) of the lesion candidate). Note that when information of the existence period RD(t) of the amotio retinae is not available from the data server 40, $R_1$ is calculated while RD(t)=1 in equation (2').

In step S430, the visual function prognosis prediction unit 1332 calculates a visual function drop risk degree $P_1$ as an index (value) associated with prognosis prediction of the visual function. This degree is an index (value) indicating a visual function drop possibility in the future. Note that RDe (x, y) is a value, which is set according to the presence/absence of the lesion candidate (amotio retinae) at each point (x, y) on the x-y plane. For example, the lesion detection unit 132 sets RDe(x, y)=1 if an amotio retinae is detected at position coordinates (x, y), and sets RDe(x, y)=0 if no amotio retinae is detected. The visual function prognosis prediction unit 1332 acquires the normal value data ($\omega$) indicating the density distribution of the photoreceptor cells and the setting data (RDe) set according to the presence/absence of the lesion candidates, and makes a calculation given by:

$$P_1 = \Sigma\{\omega(a) \cdot RDe(x,y)\} \qquad (3)$$

If the existence period RD(t) of the amotio retinae at each point (x, y) on the x-y plane is available, an estimated value $P_1'$ of a visual function drop time can be generated by:

$$P_1' = \Sigma\{\omega(a) \cdot (Td - RD(t))\} \qquad (3')$$

where Td is data indicating a maximum survival period of the photoreceptor outer segment without any nutrient supply from a choroid coat, and can be acquired from the data server 40 or storage unit 120.

(Diagnosis Support Information Output Processing)

Figure 5:
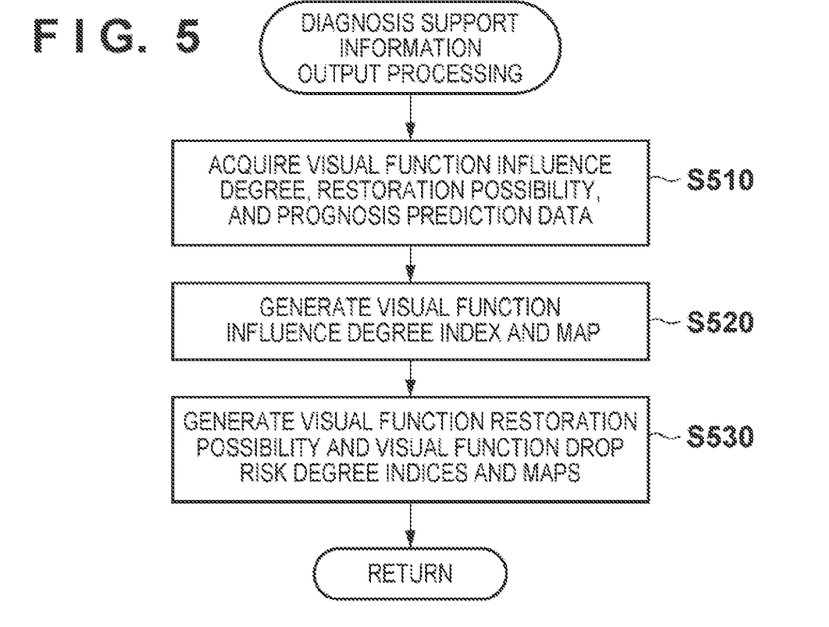
FIG. 5 is a flowchart showing details of processing executed in step S250 according to the first embodiment.

Details of the processing executed in step S250 will be described below with reference to FIG. 5.

In step S510, the diagnosis support information output unit 140 acquires data associated with the visual function influence degrees, visual function restoration possibilities, and visual function drop risk degrees from the image processing unit 130. Then, the diagnosis support information output unit 140 transmits the respective pieces of information to the visual function influence degree information output unit 141, visual function restoration possibility information output unit 142, and visual function prognosis prediction information output unit 143.

In step S520, the visual function influence degree information output unit 141 generates a map having, as values, influence degrees on the visual function at respective points on the x-y plane, which are calculated in step S410, that is, ω(a)·Tn/Tp(x, y). This map visualizes the influence degrees on the visual function, and represents the visual function influence degrees at respective points (x, y) at the image capturing timing. On the monitor 1205 (FIG. 12), not only the visual function influence degree map but also the influence degree $S_1$ calculated in step S410 is output at the same time.

In step S530, the visual function restoration possibility information output unit 142 generates a map having values ((Tp(x, y)/Tn)·(1/RD(t)) or 0) of the visual function restoration possibilities at respective points on the x-y plane, which are calculated in step S420. Also, the visual function prognosis prediction information output unit 143 generates a map having values (ω(a)·RDe(x, y)) of the visual function drop risk degrees, which are calculated in step S420.

In this case, when the existence periods RD(t) of the amotio retinae at respective points (x, y) on the x-y plane are available, a map having, as values, estimated values of the visual function drop times at the respective points (x, y), that is, ω(a)·(Td−RD(t)), is generated. Note that Td represents a maximum survival period of the photoreceptor outer segment without any nutrient supply from a choroid coat.

On the monitor 1205, in addition to the aforementioned maps, the index $R_1$ associated with the visual function restoration possibility, the index $P_1$ associated with the visual function drop risk degree, and the index $P_1'$ associated with the visual function drop time estimated value can also be output.

According to this embodiment, the image processing apparatus calculates values indicating the influence degrees on the visual function according to the positional relationship between the thinned region of the photoreceptor outer segment thicknesses and the fovea centralis. Also, the image processing apparatus checks the presence/absence of an amotio retinae, and also calculates the visual function drop risk degrees using information indicating the photoreceptor outer segment thicknesses and the presence/absence of the amotio retinae. Thus, the image processing apparatus can predict the influence of the lesion candidates on the visual function and the prognosis of the visual function from the tomogram of a macular disease.

(Second Embodiment)

This embodiment will examine a case in which exudative lesions such as leukomas EX are collected under a fovea centralis F1 as a case of the influence imposed on the visual function in place of layer shape anomalies unlike in the first embodiment. The leukomas EX are extracted, and the influence on the visual function and the prognosis of the visual function are predicted based on the positional relationship between a distribution of the leukomas EX and ophthalmic features such as the fovea centralis F1.

The configuration of apparatuses connectable to the image processing apparatus 10 according to this embodiment and the functional arrangement of the image processing apparatus 10 are the same as those in the first embodiment. Also, the image processing sequence of this embodiment is the same as that (FIG. 2) in the first embodiment, except for processes in steps S230, S240, and S250 in FIG. 2. Hence, only the processes in steps S230, S240, and S250 will be described below.

Figure 6:
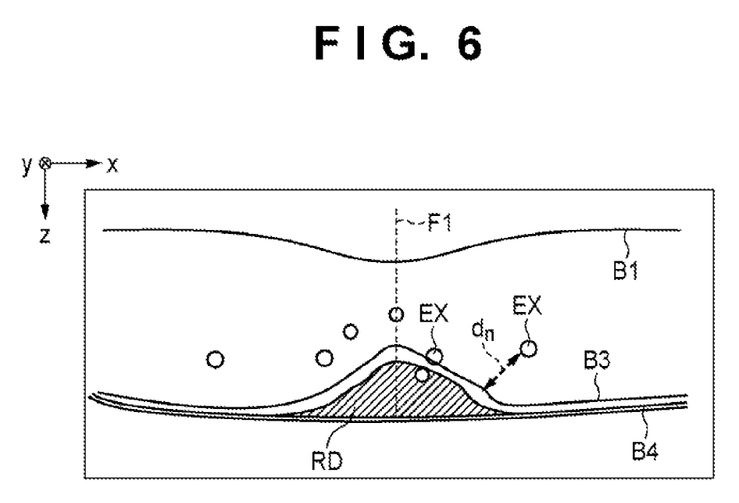
FIG. 6 is a view for explaining the image processing contents in the second embodiment.

As shown in FIG. 6, massive high-luminance regions called leukomas EX are formed in a retina that suffers a retinopathy of diabetes, since fat and protein leaking from retinal blood vessels are collected. The leukomas EX are normally formed in the vicinity of an outer plexiform layer. Since locations of the leukomas EX shield incoming light and light cannot reach photoreceptor cells C1, a visual acuity decreases. Especially, as the locations of the leukomas EX are closer to the fovea centralis F1, the influence on the visual function is serious due to a high petrosal density.

If an amotio retinae RD exists below the fovea centralis F1, it is empirically known that leukomas EX tend to be collected toward the amotio retinae RD. Once the leukomas EX are collected below the fovea centralis F1, a visual acuity considerably lowers, and recovery of the visual acuity cannot be expected. Therefore, it is helpful to know distances between the leukomas EX and subretina and whether or not the leukomas EX move toward the subretina for the purpose of prevention of a visual function drop due to collection of lesions below the fovea centralis.

(Processing in Step S230)

In the processing in step S230 in the second embodiment, the lesion detection unit 132 detects leukomas EX in an ophthalmic tomogram as lesion candidates. In this case, the leukomas EX are identified as follows by combining information of luminance values and output values of a filter such as a point convergence filter, which emphasizes massive structures. That is, a region where an output of the point convergence filter is equal to or larger than a threshold Ta and a luminance value on a tomogram is equal to or larger than a threshold Tb is identified as a leukoma EX. Note that the detection method of the leukomas EX is not limited to this, and an arbitrary known lesion detection method can be used. Also, as in the first embodiment, the presence/absence of an amotio retinae RD is detected within a region sandwiched between the boundary B3 between photoreceptor inner and outer segments and the retinal pigment epithelium boundary B4 detected in step S220.

Next, the lesion detection unit 132 quantitates a distribution of the leukomas EX in the retina based on the detected lesions (leukomas EX and amotio retinae RD). More specifically, the lesion detection unit 132 labels the detected leukomas EX. As a result of labeling, label values are respectively set for the leukomas EX. In this case, a region expansion method is used as the labeling method. Note that the labeling method is not limited to this, and an arbitrary known labeling method can be used. Next, a volume of the leukomas EX having the same label value is calculated. When the amotio retinae RD exists in the retina, a shortest distance do of a leukoma EX of a label n to the amotio retinae RD is calculated.

(Processing in Step S240)

Details of the processing to be executed in step S240 of the second embodiment will be described below with reference to FIG. 6 and the flowchart shown in FIG. 4.

In step S410, the visual function influence degree determination unit 133 calculates a value $S_2$ indicating an influence degree on the visual function using equation (4) below. In this case, a visual acuity will be examined as the visual function.

$$S_2 = \Sigma n \Sigma \text{area}\{\omega(a)\} \quad (4)$$

where ω(a) is a petrosal density [the number of cells/mm$^2$] which is the same as that in the first embodiment, area represents an area when leukomas EX having the same label are projected onto the x-y plane, and n represents the number of leukomas EX which exist within an image capturing region.

In step S420, the visual function restoration function possibility determination unit 1331 calculates an index $R_2$ associated with a visual function restoration possibility using:

$$R_2 = \Sigma n\{\omega(a) \cdot d_n\} \quad (5)$$

where n is the total number of detected leukomas EX, $v_n$ is a volume of leukomas EX of a label n, and $d_n$ is a distance between the barycentric point of the leukomas EX of the label n and the amotio retinae RD.

In step S430, the visual function prognosis prediction unit 1332 calculates a visual function drop risk degree, that is, a lesion collection risk degree $P_2$ under the fovea centralis F1 using:

$$P_2 = \Sigma n\{v_n/(d_n+1)\} \quad (6)$$

(Processing in Step S250)

Details of the processing to be executed in step S250 will be described below with reference to FIG. 5. Note that since step S510 is the same as that in the first embodiment, a description thereof will not be repeated.

In step S520, the visual function influence degree information output unit 141 generates a map (visual function influence degree map) having values indicating influence degrees on the visual function at respective points (x, y) on the x-y plane, which are calculated in step S410. On the monitor 1205 shown in FIG. 12, not only the visual function influence degree map, but also the value $S_2$ indicating the visual function influence degree calculated in step S410 can be output at the same time.

In step S530, the visual function restoration possibility information output unit 142 and visual function prognosis prediction information output unit 143 generate a map having values indicating visual function restoration possibilities at respective points on the x-y plane, which are calculated in step S420, and a map having values indicating visual function drop risk degrees, which are calculated in step S430. Furthermore, on the monitor 1205 shown in FIG. 12, not only the visual function restoration possibility map and visual function drop risk degree map, but also the index $R_2$ associated with the visual function restoration possibility and the visual function drop risk degree $P_2$ can be output at the same time.

With the aforementioned arrangement, the image processing apparatus 10 extracts the leukomas EX and amotio retinae RD as lesions, and can predict the influence on the visual function and the prognosis of the visual function based on the positional relationships with the ophthalmic features such as the fovea centralis F1.

(Third Embodiment)

This embodiment will examine a case in which the influence on the visual function appears due to a shape anomaly of a tissue called a cribrosa lamina L3, which exists in a deep layer of an optic papilla unlike in the first embodiment. Extraction and shape measurement of layer boundaries and the cribrosa lamina L3 in a retina are made, and the influence on the visual function and the prognosis of the visual function are predicted using information of positional relationships with ophthalmic features such as a Mariotte blind spot in addition to a fovea centralis F1.

Figure 7A:
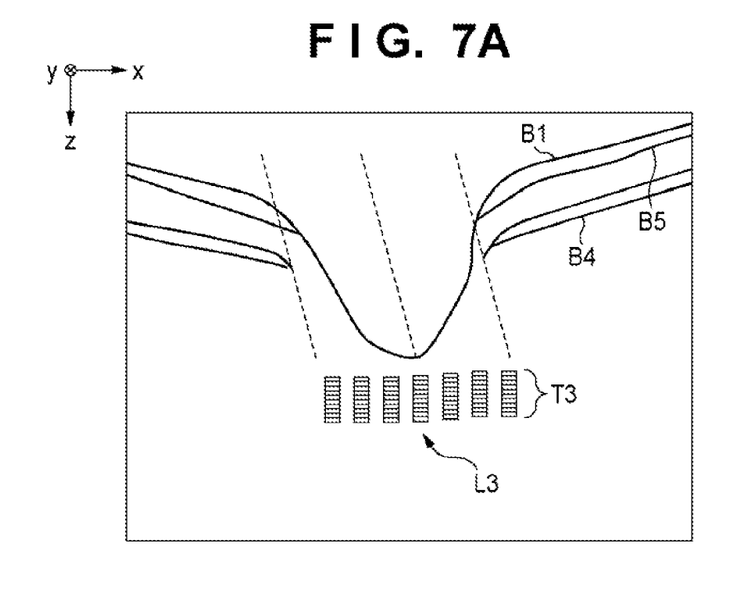
FIGS. 7A and 7B are views for explaining the image processing contents in the third embodiment.
Figure 7B:
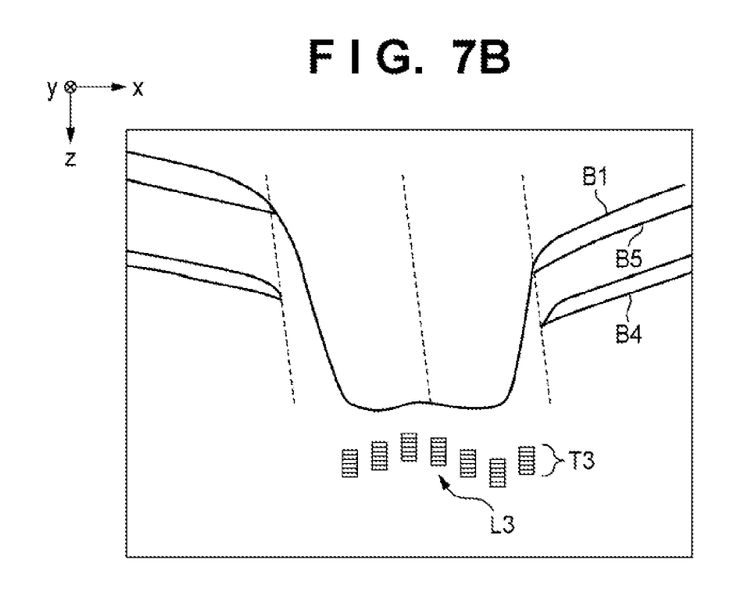

As shown in FIGS. 7A and 7B, a cribrum-shaped film called a cribrosa lamina L3 exists below the optic papilla. The cribrosa lamina L3 has a disc shape when viewed from a direction perpendicular to the x-y plane, and about 600 to 700 pores are formed. Optic nerve fiber bundles, that is, sets of axons of photoreceptor cells C1 pass through these pores, and are extended toward a brain. When an intraocular pressure rises, the cribrosa lamina L3 is deflected to dislocate pore positions, and to press the axons, resulting in extinction of the photoreceptor cells C1.

The configuration of apparatuses connectable to the image processing apparatus 10 according to this embodiment is the same as that of the first embodiment. Also, the functional arrangement of the image processing apparatus 10 is the same as that of the first embodiment, except that the visual function influence degree determination unit 133 does not include the visual function restoration possibility determination unit 1331, and the diagnosis support information output unit 140 does not include the visual function restoration possibility information output unit 142. This reflects that once the photoreceptor cells C1 have become extinct to impose the influence on the visual function, the visual function can no longer be restored. The image processing sequence of this embodiment is the same as that (FIG. 2) of the first embodiment, except for the processes in steps S220, S230, S240, and S250 shown in FIG. 2. Hence, only the processes in steps S220, S230, S240, and S250 will be explained below.

(Processing in Step S220)

In the processing in step S220 in the third embodiment, the ophthalmic feature acquisition unit 131 detects an optic papilla and fovea centralis F1 by detecting a fovea from a tomogram. Furthermore, the ophthalmic feature acquisition unit 131 extracts retinal blood vessels in a projected image of the tomogram, and determines a portion including the retinal blood vessels as the optic papilla, and a portion without including any retinal blood vessels as the fovea centralis F1. The retinal blood vessel extraction method uses an arbitrary known line emphasis filter. The optic papilla fovea is unperceivable and is called a Mariotte blind spot since it does not include any photoreceptor cells C1.

Next, the ophthalmic feature acquisition unit 131 acquires an inner limiting membrane B1, nerve fiber layer boundary B5, and retinal pigment epithelium boundary B4 as layer boundaries. The layer boundary extraction method is the same as that in the first embodiment, and a description thereof will not be repeated. Furthermore, the ophthalmic feature acquisition unit 131 detects the cribrosa lamina L3 in the following sequence. That is, at respective points (x, y) in a region (Mariotte blind spot) where no retinal pigment epithelium boundary B4 exists on the x-y plane, a high-luminance region which is located on the deep layer side of the inner limiting membrane B1 (on the positive direction side of the z axis) and in which luminance values are equal to or higher than a certain threshold Tx is detected. The cribrosa lamina L3 is detected as a porous disc-shaped region on the x-y plane. In this embodiment, the nerve fiber layer boundary B5 is used. Instead, an inner plexiform layer boundary B2 may be acquired. However, in this case, GCC (Ganglion Cell Complex) thicknesses are measured in step S230 in place of the nerve fiber layer thicknesses.

(Processing in Step S230)

In the processing in step S230 in the third embodiment, the lesion detection unit 132 measures nerve fiber layer thicknesses using the inner limiting membrane B1 and nerve fiber layer boundary B5 acquired in step S220. Next, the lesion detection unit 132 acquires a normal value range of the nerve fiber layer thicknesses from the data server 40, and detects points (x', y') outside the Mariotte blind spot, which have the nerve fiber layer thicknesses falling outside the normal value range, as lesion locations. Furthermore, the lesion detection unit 132 measures cribrosa lamina thicknesses and roughened patterns of a cribrosa lamina boundary, and detects points (x, y) inside the Mariotte blind spot, which fall outside normal value ranges of the cribrosa lamina thicknesses and roughened patterns that are acquired from the data server 40, as lesion locations.

(Processing in Step S240)

Figure 8:
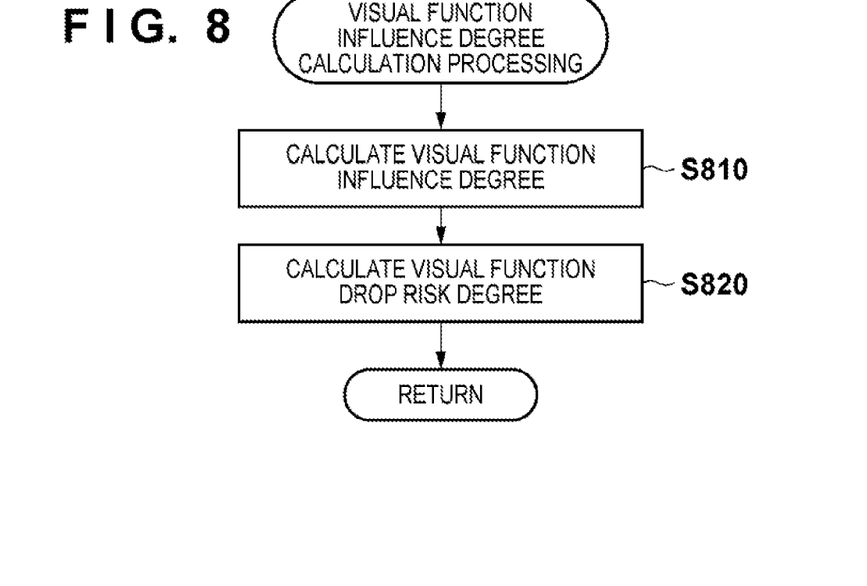
FIG. 8 is a flowchart showing details of processing executed in step S240 according to the third embodiment.

Details of the processing executed in step S240 will be described below with reference to FIG. 8. In step S810, the visual function influence degree determination unit 133 calculates a value $S_3$ indicating a visual function influence degree from the nerve fiber layer thicknesses acquired in step S230 according to:

$$S_3 = \Sigma x, y\{B\} \quad (7)$$

$$B = \begin{cases} \alpha(x, y) \cdot T_{n(x,y)} / T_{1(x,y)} & \text{(outside fovea centralis)} \\ 1 & \text{(fovea centralis)} \end{cases}$$

where $T_{n(x,y)}$ is a normal value (median thereof) of the nerve fiber layer thickness at the point (x, y) on the x-y plane. $T_{1(x,y)}$ is the nerve fiber layer thickness at the point (x, y) on the x-y plane, which is determined as a nerve fiber layer thickness anomaly in step S230. $\alpha(x, y)$ is a variable which assumes 0 at a central Mariotte blind spot, or 1 at other spots.

In step S820, the visual function prognosis prediction unit 1332 calculates a visual function drop risk degree $P_3$ from the thicknesses and roughened patterns of the cribrosa lamina L3 acquired in step S230 according to:

$$P_3 = \Sigma x, y(T_{ns}/T_s) + k \cdot \Sigma y \Sigma x\{\Pi/\theta_{x,y}\} \quad (8)$$

where $\theta_{x,y}$ is an angle [rad] three neighboring points (three points x−1, x, and x+1 in the x-axis direction, and three points y−1, y, and y+1 in the y-axis direction) of control points that configure the boundary of the cribrosa lamina make. Also, k is a proportional constant.

(Processing in Step S250)

Figure 9:
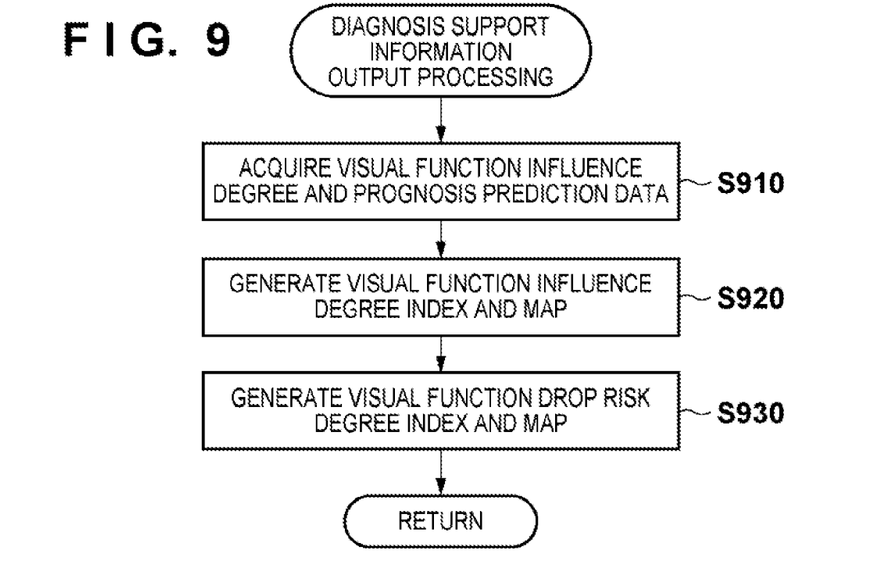
FIG. 9 is a flowchart showing details of processing executed in step S250 according to the third embodiment.

Details of the processing executed in step S250 will be described below with reference to FIG. 9.

In step S910, the diagnosis support information output unit 140 acquires data associated with the visual function influence degrees and visual function drop risk degrees from the image processing unit 130, and transmits them to the visual function influence degree information output unit 141 and visual function prognosis prediction information output unit 143, respectively.

In step S920, the visual function influence degree information output unit 141 generates a map (visual function influence degree map) having values indicating influence degrees on the visual function at respective points (x, y) on the x-y plane, which are calculated in step S810. On the monitor 1205 shown in FIG. 12, not only the visual function influence degree map but also the index (value) of the visual function influence degree calculated in step S810 can also be output at the same time.

In step S930, the visual function prognosis prediction information output unit 143 generates a map having values indicating visual function drop risk degrees at respective points on the x-y plane, which are calculated in step S820. Furthermore, on the monitor 1205 shown in FIG. 12, not only the visual function drop risk degree map but also the visual function drop risk degree calculated in step S820 can also be output at the same time.

According to the aforementioned arrangement, the image processing apparatus 10 extracts a shape anomaly (thinned or roughened) region of the cribrosa lamina in the optic papilla, and calculates visual function influence degrees and visual function drop risk degrees in accordance with the positional relationships with the fovea centralis and Mariotte blind spot. Thus, in a case of an early glaucoma, the influence on the visual function and the prognosis of the visual function can be predicted based on the distribution of lesions below the retina from an ophthalmic tomogram of the optic papilla.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-020089, filed Feb. 1, 2011, which is hereby incorporated by reference herein in its entirety.

What is claimed is:

1. An image processing apparatus comprising:
an acquisition unit configured to acquire a tomogram of an eye portion of a patient to be examined;
an information acquisition unit configured to acquire information of a predetermined portion and position information of a predetermined tissue structure from the tomogram and an existence period of a lesion candidate to be included in the tissue structure; and
a calculation unit configured to calculate an evaluation value associated with a visual function based on the existence period of the candidate and a relationship between the information of the predetermined portion and a position of the predetermined tissue structure.

2. The apparatus according to claim 1, wherein the information of the predetermined portion is information of a density distribution of photoreceptor cells in the tomogram, and
wherein said calculation unit calculates the evaluation value based on the density distribution of the photoreceptor cells in the predetermined tissue structure.

3. The apparatus according to claim 2, wherein the predetermined tissue structure is a region of an amotio retinae.

4. The apparatus according to claim 1, wherein the information of the predetermined portion is information of a density distribution of photoreceptor cells in the tomogram, and
said calculation unit calculates the evaluation value based on a thickness distribution of the predetermined tissue structure.

5. The apparatus according to claim 4, wherein the predetermined tissue structure is a region between a boundary between photoreceptor inner and outer segments and a retinal pigment epithelium boundary.

6. The apparatus according to claim 1, wherein the predetermined portion is a portion below a fovea centralis, and
wherein said calculation unit calculates the evaluation value based on a positional relationship with the predetermined tissue structure.

7. The apparatus according to claim 6, wherein the predetermined tissue structure is a leukoma.

8. The apparatus according to claim 1, wherein the predetermined portion is a Mariotte blind spot, and
wherein said calculation unit calculates the evaluation value based on a positional relationship with the predetermined tissue structure.

9. The apparatus according to claim 8, wherein the predetermined tissue structure is a cribrosa lamina.

10. The apparatus according to claim 3, wherein said calculation unit calculates, as the evaluation value, a restoration possibility of a visual function of the eye portion from an existence period of the amotio retinae.

11. The apparatus according to claim 1, wherein said calculation unit calculates the evaluation values in association with two-dimensional coordinates of the tomogram, and wherein said apparatus further comprises a display control unit configured to display the evaluation values associated with the two-dimensional coordinates of the tomogram as a map on a display unit.

12. An image processing method of an image processing apparatus, said method comprising:

an acquisition step of acquiring a tomogram of an eye portion of a patient to be examined;

an information acquisition step of acquiring information of a predetermined portion and position information of a predetermined tissue structure from the tomogram, and an existence period of a lesion candidate to be included in the tissue structure; and a calculation step of calculating an evaluation value associated with a visual function based on the existence period of the lesion candidate and a relationship between the information of the predetermined portion and a position of the predetermined tissue structure.

13. A non-transitory computer readable storage medium storing a program for controlling a computer to execute respective steps of an image processing method according to claim 12.

* * * * *